(12) United States Patent
Steinbacher

(10) Patent No.: US 9,261,453 B2
(45) Date of Patent: Feb. 16, 2016

(54) METHOD AND GAS ANALYZER FOR MEASURING THE CONCENTRATION OF A GAS COMPONENT IN A SAMPLE GAS

(71) Applicant: Siemens Aktiengesellschaft, Munich (DE)

(72) Inventor: Franz Steinbacher, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/486,765

(22) Filed: Sep. 15, 2014

(65) Prior Publication Data

US 2015/0085288 A1 Mar. 26, 2015

(30) Foreign Application Priority Data

Sep. 25, 2013 (EP) ................................. 13185868

(51) Int. Cl.
*G01N 21/00* (2006.01)
*G01N 21/39* (2006.01)
*G01N 33/00* (2006.01)
*G01J 3/433* (2006.01)

(52) U.S. Cl.
CPC ................. *G01N 21/00* (2013.01); *G01J 3/433* (2013.01); *G01N 21/39* (2013.01); *G01N 33/0062* (2013.01); *G01J 2003/4334* (2013.01); *G01N 2201/0691* (2013.01)

(58) Field of Classification Search
CPC .... G01N 21/274; G01N 21/031; G01N 21/31
USPC ....................... 356/433–437, 243.1
See application file for complete search history.

(56) References Cited

U.S. PATENT DOCUMENTS

| | | | |
|---|---|---|---|
| 8,094,313 B2 * | 1/2012 | Kluczynski | G01J 3/4338 356/437 |
| 2004/0223158 A1 | 11/2004 | Lundqvist et al. | |
| 2012/0287418 A1* | 11/2012 | Scherer | G01N 21/61 356/51 |

FOREIGN PATENT DOCUMENTS

DE 102012202893 1/2013
EP 1475618 12/2008

OTHER PUBLICATIONS

Cassidy D T et al; ""Harmonic Detection with Tunable Diode Lasers—Two-Tone Modulation""; Publisher: Springer-Verlag; vol. 829, No. 4; pp. 279-285; XP008047327; 1982; CA; Dec. 1, 1982.

* cited by examiner

*Primary Examiner* — Kara E Geisel
*Assistant Examiner* — Iyabo S Alli
(74) *Attorney, Agent, or Firm* — Cozen O'Connor

(57) ABSTRACT

Gas analyzer and method for measuring the concentration of a gas component in a sample gas, wherein the wavelength of the light of a wavelength-tunable light source is varied within periodically successive sampling intervals and, in the process, additionally modulated with a frequency to perform wavelength dependent sampling of an absorption line of a gas component to be measured in the sample gas.

8 Claims, 4 Drawing Sheets

METHOD AND GAS ANALYZER FOR MEASURING THE CONCENTRATION OF A GAS COMPONENT IN A SAMPLE GAS

BACKGROUND OF THE INVENTION

1. Field of the Invention

The invention relates to a gas analyzer and method for measuring the concentration of a gas component in the gas analyzer.

2. Description of the Related Art

EP 1 475 618 B1 discloses a conventional method and gas analyzer.

The known gas analyzer is a laser spectrometer which, in particular, is used for optical gas analysis in process metrology. A wavelength-tunable light source comprising a laser diode generates light in the infrared range, which is guided through a process gas (sample gas) to be measured and subsequently detected. The wavelength of the light is tuned to a specific absorption line of the respective gas component to be measured, where the laser diode samples the absorption line periodically in a wavelength-dependent manner. To this end, the laser diode is actuated by a ramp-shaped or triangular current signal within periodically successive sampling intervals. During the comparatively slow sampling of the absorption line, the wavelength of the generated light is additionally modulated sinusoidally with a high frequency and small amplitude. The profile of the absorption line is nonlinear. As a result, harmonics above the modulation frequency are also generated in the measurement signal obtained during the detection. The measurement signal is usually demodulated at an n-th overtone, preferably the second harmonic, using a phase-sensitive lock-in technology and evaluated to form a measurement result for each sampling interval. In the case of a small modulation amplitude, the detection of the n-th harmonic is directly proportional to the n-th derivative of the direct measurement signal. By way of example, the evaluation is brought about by fitting (i.e., curve fitting) the profile of the demodulated measurement signal (i.e., intended curve), to be expected in the ideal case, to the actual profile (i.e., actual curve) thereof. Finally, the concentration of the gas component to be measured is determined from the measurement result obtained in the process.

The detection and determination limit for measuring the concentration of the gas component are restricted by the noise of the gas analyzer (e.g., laser noise, and/or detector noise), which is superposed on the measurement signal.

SUMMARY OF THE INVENTION

It is therefore an object of the invention to improve invention the measurement signal-to-noise ratio when measuring the concentration of the gas component in a sample gas.

This and other objects and advantages are achieved in accordance with the invention by providing a method and gas analyzer in which the wavelength of the light of the light source is modulated not only with one frequency but with a plurality of frequencies $(2n-1)f$, where $n=1, 2, 3 \ldots$. The measurement signal is demodulated at the second harmonic $2(2n-1)f$ of these frequencies or, as explained further below, at the frequencies $2nf$. By way of example, the demodulated measurement signals obtained in the process are combined by data fusion (e.g., data fusion, or multi-sensor data fusion), added in the simplest case, and then furthermore evaluated to form a measurement result, e.g., by curve evaluation, curve fitting or correlation with reference signals. Alternatively, the demodulated measurement signals can initially be evaluated individually and the obtained measurement results can subsequently be combined, such as added.

As a result of the nonlinear form of the absorption line, the measurement signal contains not only the multiples (i.e., harmonics) of the frequencies used during the modulation but also the sums and differences of these frequencies. The modulation frequencies are separated by twice the magnitude of the smallest modulation frequency f and the demodulation of the measurement signal occurs at the second harmonics of the modulation frequencies. As a result, the sum and difference frequencies either coincide with the second harmonic of the modulation frequencies or lie exactly halfway between these, and so the frequency components of the measurement signal lie spaced apart by twice the magnitude of the smallest modulation frequency f and hence by twice the signal bandwidth. Each of the amplitudes of the frequencies above the second harmonic are significantly smaller than those of the second harmonic and are therefore not bothersome. Hence, the following frequency components emerge in the measurement signal when modulating the wavelength of the light with, e.g., four different frequencies f, 3f, 5f, 7f:

2f: second harmonic of the measurement signal component resulting from the modulation frequency f,
    difference between the modulation frequencies 3f and f,
    difference between the modulation frequencies 5f and 3f,
    difference between the modulation frequencies 7f and 5f;
4f: difference between the modulation frequencies 5f and f,
    difference between the modulation frequencies 7f and 3f,
    sum of the modulation frequencies f and 3f;
6f: second harmonic of the measurement signal component resulting from the modulation frequency 3f,
    difference between the modulation frequencies 7f and f,
    sum of the modulation frequencies f and 5f;
8f: sum of the modulation frequencies f and 7f,
    sum of the modulation frequencies 3f and 5f;
10f: second harmonic of the measurement signal component resulting from the modulation frequency 5f,
    sum of the modulation frequencies 3f and 7f;
12f: sum of the modulation frequencies 5f and 7f;
14f: second harmonic of the measurement signal component resulting from the modulation frequency 7f.

The noise in the different frequency bands is not correlated and the different signal components at the frequencies 2f to 14f are added. As a result, a very high signal-to-noise ratio is generated during the evaluation to form the measurement result.

Preferably, all measurement signal components with the frequencies 2f to 14f are used for the evaluation. However, it is also possible to use only the measurement signal components with the second harmonics 2f, 6f, 10f, 14f resulting from the modulation frequencies f, 3f, 5f, 7f. Moreover, in each case, the evaluation can be restricted to the best frequency bands in the case of interferences.

As mentioned previously, the demodulated measurement signals can initially be added and then evaluated to form the measurement result or initially evaluated individually and the obtained measurement results can subsequently be added. If the noise is not correlated in the two variants, both variants can be calculated and added, which may lead to a further improvement in the signal-to-noise ratio. The individual evaluation of the demodulated measurement signals is advantageous in that the different frequency modulations can be corrected or adapted depending on the individual measurement results. However, incidentally, a simulation has shown that the sum of the demodulated measurement signals can be fitted well and the result is not substantially worse than that of the added individual fitted results.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

For a further explanation of the invention, reference is made to the figures in the drawing in the following text, in which.

DETAILED DESCRIPTION OF THE PREFERRED EMBODIMENTS

Figure 1:
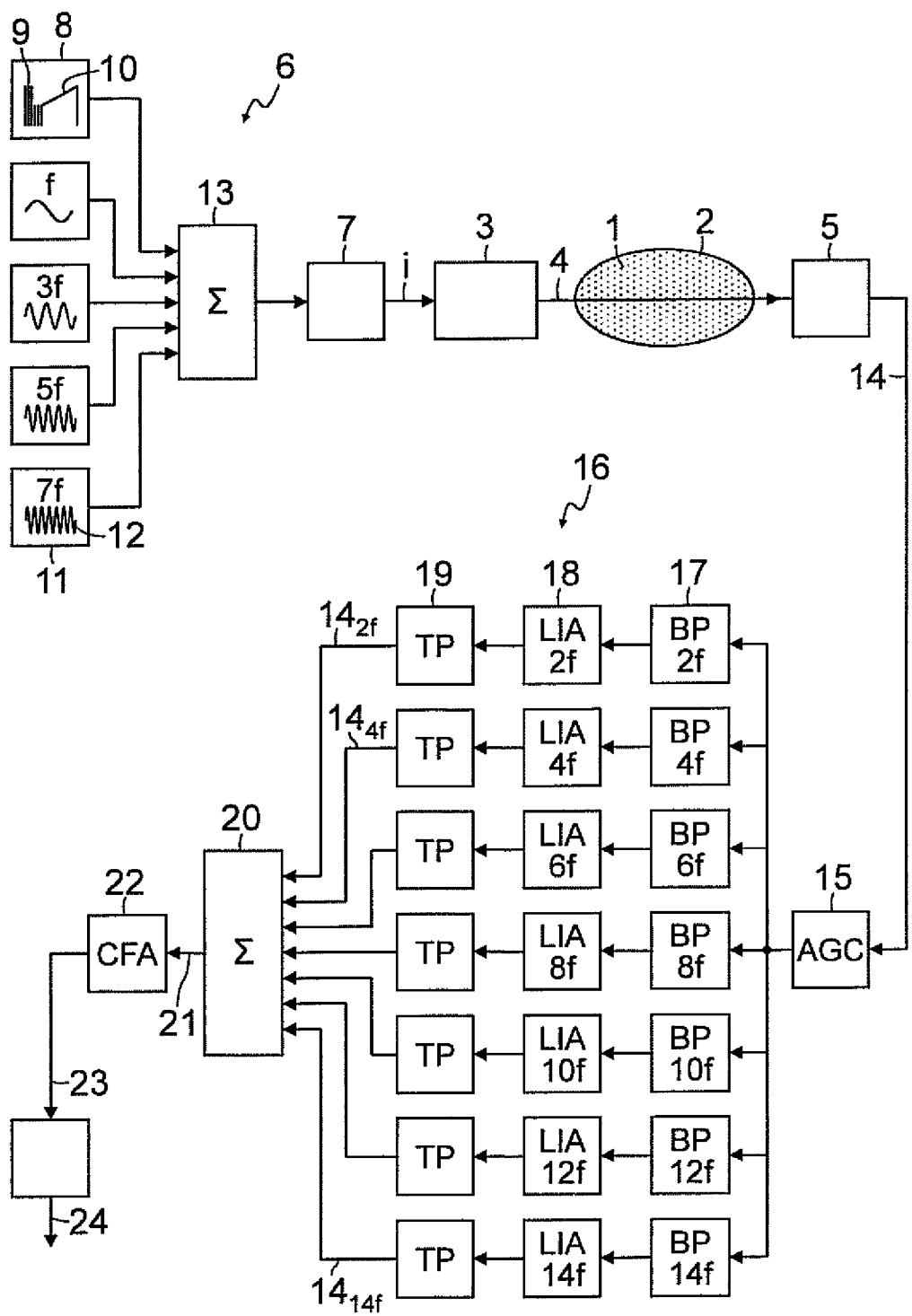
FIG. 1 shows a first exemplary embodiment of the gas analyzer in accordance with the invention.

The gas analyzer, shown in FIG. 1 in the form of a simplified block diagram, is a laser spectrometer for measuring the concentration of at least one gas component of interest of a sample gas 1 contained in a measurement volume 2, such as a measurement cuvette or a process gas line. The spectrometer contains a light source 3 in the form of a laser diode, the light 4 of which is incident on a detector 5 after passing through the sample gas 1. A current source 7 that is controlled by a modulation apparatus 6 feeds the laser diode 3 with an injection current i, where the intensity and wavelength of the generated light 4 depend on the current i and the operating temperature of the laser diode 3. The modulation apparatus 6 comprises a first signal generator 8, which periodically actuates the current source 7 with a predefined, preferably ramp-shaped or triangular function 9 to sample a selected absorption line of the gas component of interest with the wavelength of the generated light 4 which follows the profile of the current i in a more or less linear manner. The first signal generator 8 continues to generate a burst signal 10 regularly, such as after each sampling period. A plurality of signal generators 11, in this case four signal generators, generate sinusoidal signals 12 with higher frequencies f, 3f, 5f, 7f, which are superposed on the ramp-shaped or triangular function 9 in an addition member 13.

Figure 2:
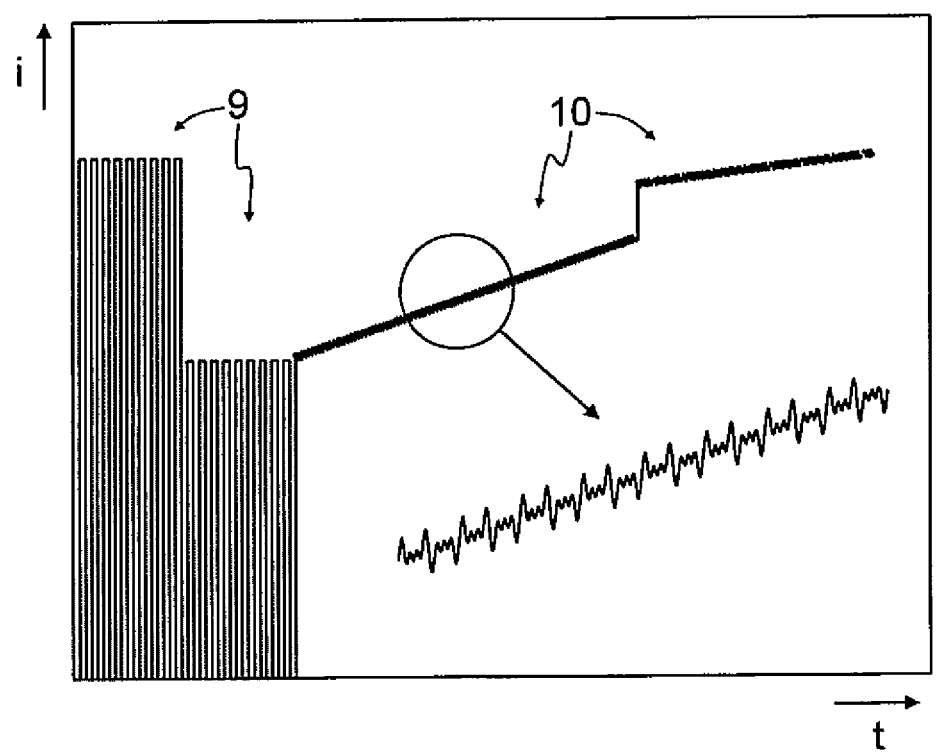
FIG. 2 shows an example for the profile of the injection current of a laser diode in the gas analyzer of FIG. 1.

FIG. 2 shows an exemplary profile of the injection current i(t) during an actuation period. Here, two different current ramps are generated via the ramp-shaped function 9 in order to be able to sample two different absorption lines, for example that of the gas component to be measured of the sample gas 1 and that of a reference gas (not depicted in FIG. 1). The current ramps are additionally modulated in a sinusoidal manner with the frequencies f, 3f, 5f, 7f and a small amplitude. Two current bursts are generated by the burst signal 10, the strength of which bursts corresponds to the initial or final value of the current ramp.

Returning to FIG. 1, the detector 5 generates a measurement signal 14 as a function of the detected light intensity, which measurement signal is high-pass filtered in an amplifier 15 and automatically amplified and normalized based on signal components resulting from the burst signal 10. In an evaluation apparatus 16, the normalized measurement signal 14 is demodulated at the second harmonic 2f, 6f, 10f, 14f of the modulation frequencies f, 3f, 5f, 7f and at the sum and difference frequencies 4f, 8f, 12f of the modulation frequencies f, 3f, 5f, 7f lying therebetween. The demodulation occurs in parallel channels, which each comprise a band-pass filter 17 and a lock-in amplifier 18 with a low-pass filter 19. In the process, the band-pass filtered measurement signal 14 is demodulated in a phase-sensitive manner by multiplication with a reference signal at the respective demodulation frequency 2f, 4f to 14f and the in-phase component, i.e., the used signal component of the demodulated measurement signal $14_{2f}$, $14_{4f}$ to $14_{14f}$, is extracted by the subsequent low-pass filtering. The demodulated measurement signals $14_{2f}$, $14_{4f}$ to $14_{14f}$, more precisely the used signal components thereof, are summed to form a sum signal 21 in an addition module 20 and subsequently evaluated in a computer unit 22. In this case, the evaluation is brought about by, e.g., fitting (i.e., curve fitting) the profile of the measurement signal demodulated at the second harmonic, which is to be expected in the ideal case, to the profile of the sum signal 21. (Not only the second harmonics of the measurement signal components resulting from the different modulation frequencies, but also the measurement signal components resulting from the differences and sums of the modulation frequencies respectively have the same profile.) Finally, the concentration 24 of the gas component to be measured is determined from the measurement result 23 obtained by the evaluation.

Figure 3:
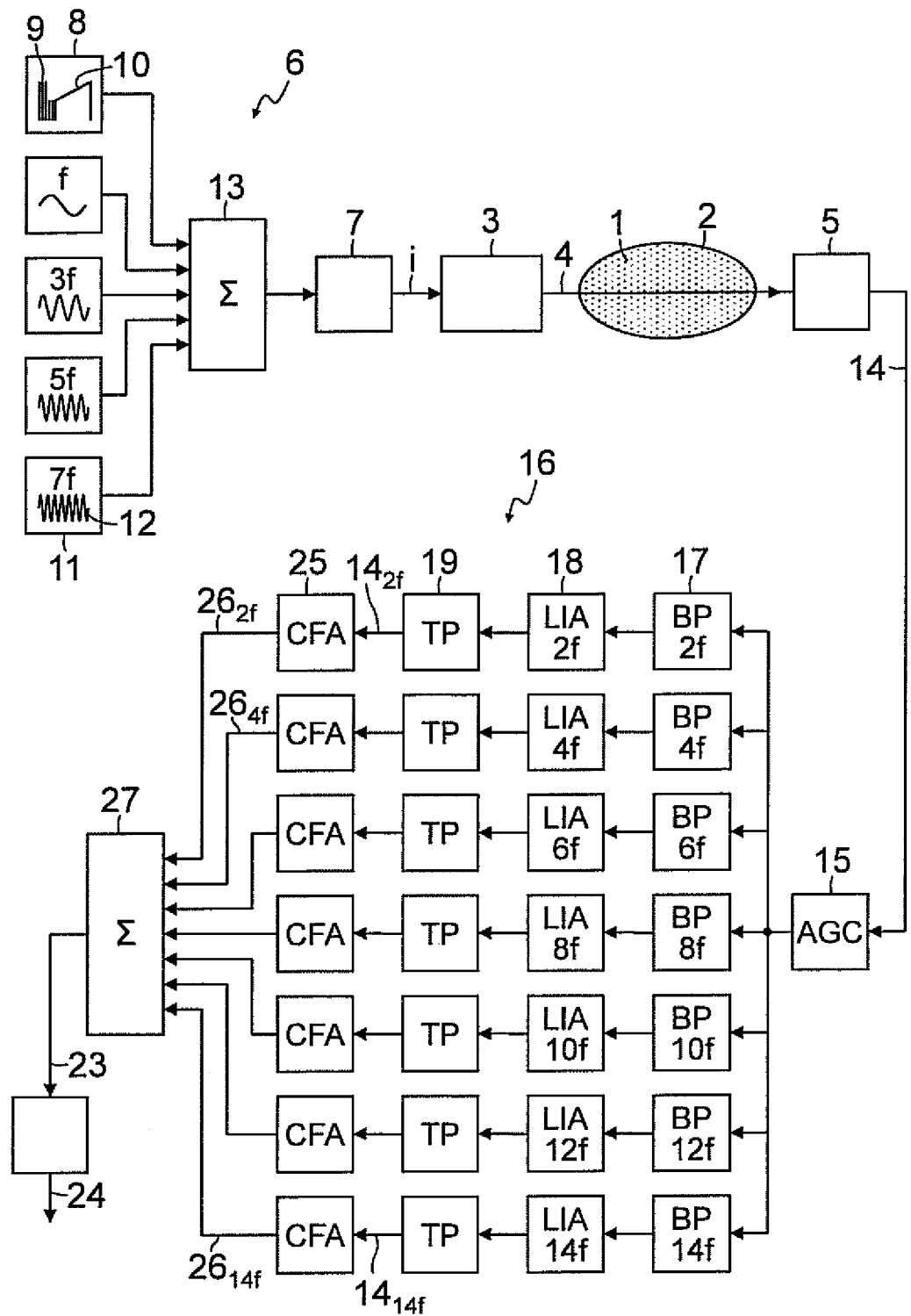
FIG. 3 shows a second exemplary embodiment of the gas analyzer according to the invention.

FIG. 3 shows an alternative exemplary embodiment of the gas analyzer in accordance with the invention, which differs from the embodiment shown in FIG. 1 in that the demodulated measurement signals $14_{2f}$, $14_{4f}$ to $14_{14f}$ or the used signal components thereof are fitted individually in computer units 25 and the results $26_{2f}$, $26_{4f}$ to $26_{14f}$ of the curve fitting are summed in an addition module 27 to form the measurement result 23.

The following provides a numerical example for designing the gas analyzer:

Digital signal processing with 192 kHz sampling rate, 6 kHz bandwidth, i.e., a frequency spacing of 12 kHz and 4 modulation frequencies f=6 kHz, 3f=18 kHz, 5f=30 kHz and 7f=42 kHz. In order to have more modulation frequencies, the signal processing would have to be analog, the sampling rate would have to be increased or the bandwidth would have to be decreased. The following frequency bands are then required on the detector side: 2f=12 kHz, 4f=24 kHz, 6f=36 kHz, 8f=48 kHz, 10f=60 kHz, 12f=72 kHz and 14f=84 kHz. These are multiples of the spacings of the modulation frequencies, i.e., in this case multiples of 2f=12 kHz. Ultimately, the number of modulation frequencies and hence the number of frequency bands depends on the utilized light source, where, currently, a VCSEL laser can be modulated with up to several hundred kilohertz.

Figure 4:
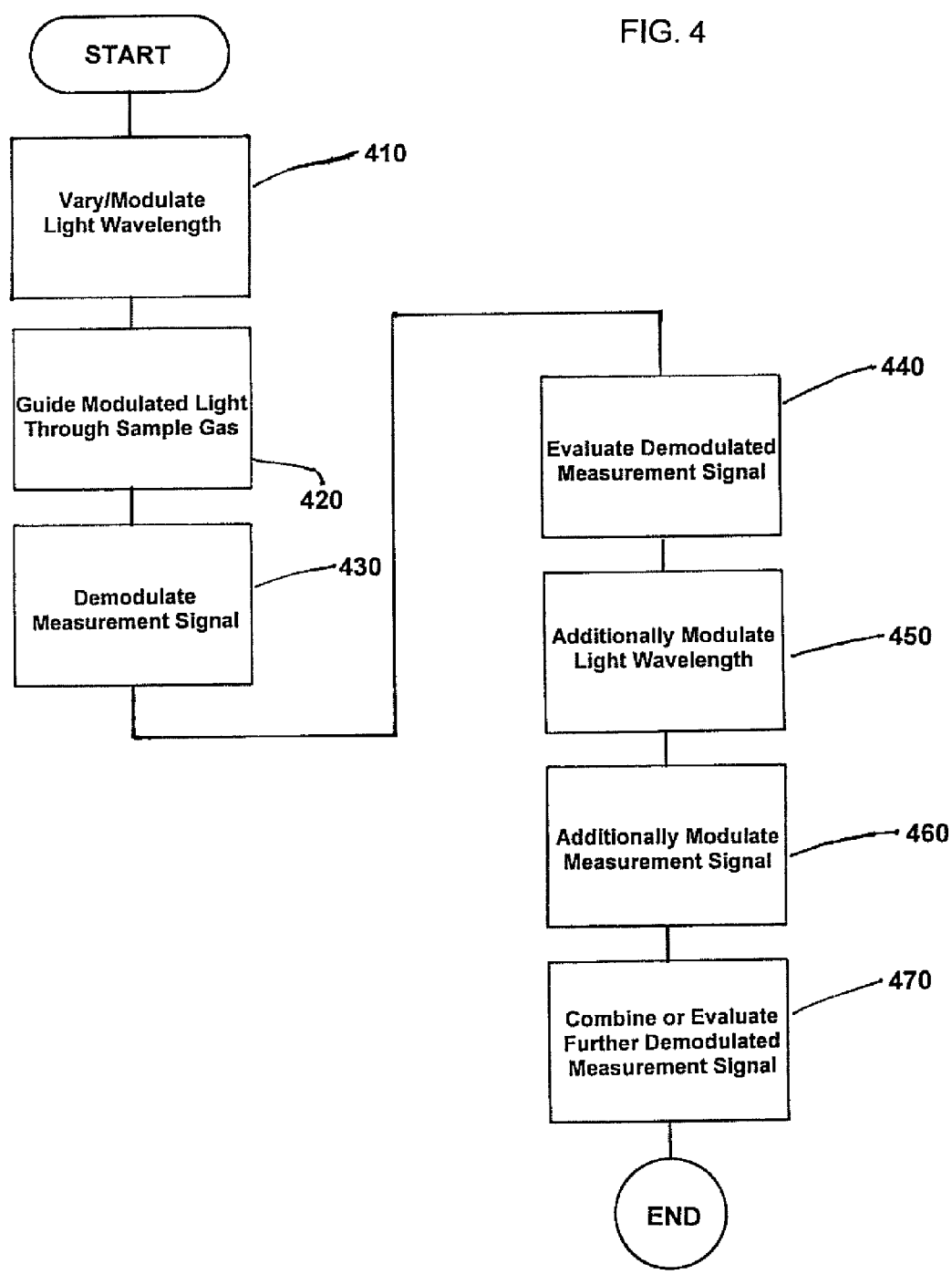
FIG. 4 is a flowchart of the method in accordance with the invention.

FIG. 4 is a method for measuring concentration of a gas component in a sample gas (1) via a gas analyzer. The method comprises varying a wavelength of light (4) of a wavelength-tunable light source (3) in periodically successive sampling intervals and, during which, sinusoidal modulation with a modulation frequency (f) is also implemented to perform wavelength-dependent sampling of an absorption line of interest of the gas component, as indicated in step 410.

Next, the modulated light (4) is guided through the sample gas (1) to a detector (5), as indicated in step 420. A measurement signal (14) generated by the detector (5) is then demodulated at a second harmonic (2f) of the modulation frequency (f), as indicated in step 430.

Next, an obtained demodulated measurement signal ($14_{2f}$) is evaluated to form a measurement result ($26_{2f}$) for each sampling interval, as indicated in step 440.

The wavelength of the light (4) of the light source (3) is additionally modulated with at least one further frequency (3f, 5f, 7f) that is greater than the next lowest further frequency or the modulation frequency (f) by twice a magnitude of the modulation frequency (f), as indicated in step 450.

Next, the measurement signal (14) is additionally modulated at the second harmonic (6f, 10f, 14f) of the at least one further frequency (3f, 5f, 7f), as indicated in step 460.

Now, at least one further obtained demodulated measurement signal ($14_{6f}$, $14_{10f}$, $14_{14f}$) is combined with the demodulated measurement signal ($14_{2f}$) or the at least one further obtained demodulated measurement signal ($14_{6f}$, $14_{10f}$, $14_{14f}$) is evaluated to form a further measurement result ($26_{6f}$, $26_{10f}$, $26_{14f}$) which is combined with the measurement result ($26_{2f}$), as indicated in step 470.

While there have been shown, described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for measuring concentration of a gas component in a sample gas via a gas analyzer, the method comprising:
    varying a wavelength of light of a wavelength-tunable light source in periodically successive sampling intervals and, during which, sinusoidal modulation with a modulation frequency is also implemented to perform wavelength-dependent sampling of an absorption line of interest of the gas component;
    guiding modulated light through the sample gas to a detector, demodulating a measurement signal generated by the detector at a second harmonic of the modulation frequency;
    evaluating an obtained demodulated measurement signal to form a measurement result for each sampling interval;
    additionally modulating the wavelength of the light of the light source with at least one further frequency which is greater than a next lowest further frequency or the modulation frequency by twice a magnitude of the modulation frequency;
    additionally demodulating the measurement signal at the second harmonic of the at least one further frequency; and
    combining at least one further obtained demodulated measurement signal with the demodulated measurement signal or evaluating the at least one further obtained demodulated measurement signal to form a further measurement result which is combined with the measurement result.

2. The method as claimed in claim 1, further comprising:
    additionally demodulating the measurement signal based on at least one of sum and difference frequencies of frequencies used for the modulation; and
    combining the at least one additional obtained demodulated measurement signal is either combined with the demodulated measurement signal or evaluating the at least one additional obtained demodulated measurement signal to form an additional measurement result which is combined with the measurement result.

3. The method as claimed in claim 1, wherein one of (i) a profile of the demodulated measurement signal is fitted to an ideal curve over a sampling interval to evaluate the demodulated measurement signal and (ii) profiles the demodulated measurement signal and the at least one further demodulated measurement signal are each fitted to an ideal curve over the sampling interval to evaluate the demodulated measurement signal and the at least one further demodulated measurement signal.

4. The method as claimed in claim 2, wherein one of (i) a profile of the demodulated measurement signal is fitted to an ideal curve over a sampling interval to evaluate the demodulated measurement signal and (ii) profiles of the at least one further demodulated measurement signal and the at least one additional demodulated measurement signal are each fitted to an ideal curve over a sampling interval to evaluate the demodulated measurement signal.

5. The method as claimed in one claim 1, wherein combining additionally demodulated measurement signals with the demodulated measurement signal is achieved by data fusion or addition.

6. The method as claimed in claim 1, wherein combining additional measurement results with the measurement result is achieved by data fusion or addition.

7. A gas analyzer for measuring the concentration of a gas component in a sample gas, comprising:
    a wavelength-tunable light source;
    a modulation apparatus which varies the wavelength of the light of the light source within periodically successive sampling intervals and simultaneously additionally modulates wavelength of the light of the light source with a modulation frequency to obtain wavelength-dependent sampling of an absorption line of interest of the gas component;
    means for guiding the modulated light through the sample gas to a detector; and
    an evaluator which demodulates a measurement signal generated by the detector at a second harmonic of the frequency and evaluates the measurement signal to form a measurement result for each sampling interval,
    wherein the modulation apparatus is configured to additionally modulate the wavelength of the light of the light source with at least one further frequency which is greater than a next lowest further frequency or modulation frequency by an amount which is twice a magnitude of the modulation frequency; and
    wherein the evaluation apparatus is configured to additionally demodulate the measurement signal at a second harmonic of the at least one further frequency and one of (i) combine at least one further obtained demodulated measurement signal with the demodulated measurement signal and (ii) evaluate the at least one further obtained demodulated measurement signal to form a further measurement result which is combined with the measurement result.

8. The gas analyzer as claimed in claim 7, wherein the evaluation apparatus is further configured to additionally demodulate the measurement signal based on at least one of sum and difference frequencies of the frequencies used for the modulation and to one of (i) combine the at least one additional obtained demodulated measurement signal with the demodulated measurement signal and (ii) evaluate the at least one additional obtained demodulated measurement signal to form an additional measurement result which is combined with the measurement result.

* * * * *